US012565493B2

(12) United States Patent
Koradin et al.

(10) Patent No.: US 12,565,493 B2
(45) Date of Patent: Mar. 3, 2026

(54) METHOD FOR PREPARING 2-[2-(2-CHLOROTHIAZOL-5-YL)-2-OXO-ETHYL]SULFANYL-6-HYDROXY-3-METHYL-5-PHENYL-PYRIMIDIN-4-ONE

(71) Applicant: BASF SE, Ludwigshafen (DE)

(72) Inventors: Christopher Koradin, Ludwigshafen (DE); Martin John McLaughlin, Liestal (CH); Roland Goetz, Ludwigshafen (DE); Rahul Kaduskar, Navi Mumbai (IN); Harish Shinde, Navi Mumbai (IN); Guillaume Michel Jacques Garivet, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 407 days.

(21) Appl. No.: 18/272,840

(22) PCT Filed: Jan. 21, 2022

(86) PCT No.: PCT/EP2022/051369

§ 371 (c)(1),
(2) Date: Jul. 18, 2023

(87) PCT Pub. No.: WO2022/157324

PCT Pub. Date: Jul. 28, 2022

(65) Prior Publication Data

US 2024/0101547 A1 Mar. 28, 2024

(30) Foreign Application Priority Data

Jan. 22, 2021 (EP) .................................... 21153040

(51) Int. Cl.
*C07D 417/12* (2006.01)

(52) U.S. Cl.
CPC .................................. *C07D 417/12* (2013.01)

(58) Field of Classification Search
CPC .................................................... C07D 417/12
See application file for complete search history.

(56) References Cited

FOREIGN PATENT DOCUMENTS

| | | | |
|---|---|---|---|
| WO | WO-2014/167084 A1 | | 10/2014 |
| WO | WO-2015/200619 A1 | | 12/2015 |
| WO | WO-2018/177970 A1 | | 10/2018 |
| WO | 2018/179541 | * | 11/2018 |
| WO | 2018/202654 | * | 11/2018 |
| WO | WO-2018/197541 A1 | | 11/2018 |
| WO | WO-2018/202654 A1 | | 11/2018 |

OTHER PUBLICATIONS

International Application No. PCT/EP2022/051369, International Search Report and Written Opinion, mailed Apr. 4, 2022.
Salvesen et al., Thiobarbiturates. Stability and formation of coordination compounds. I. Syntheses of 2-thiobarbituric acids, Norsk Farmaceutisk Selskap, Meddelelser, 25(1):1-11 (1963).
European Patent Application No. 21153040.7, Extended European Search Report, mailed May 7, 2021.

* cited by examiner

*Primary Examiner* — D Margaret M Seaman
(74) *Attorney, Agent, or Firm* — MARSHALL, GERSTEIN & BORUN LLP

(57) ABSTRACT

The present invention relates to a method for preparing 2-[2-(2-chlorothiazol-5-yl)-2-oxo-ethyl]sulfanyl-6-hydroxy-3-methyl-5-phenyl-pyrimidin-4-one or a tautomer thereof, to 2-[2-(2-chlorothiazol-5-yl)-2-oxo-ethyl]sulfanyl-6-hydroxy-3-methyl-5-phenyl-pyrimidin-4-one or a tautomer thereof and to its use as intermediate in the preparation of 2,3-dihydrotheiazolo[3,2-a]pyrimidinium compounds, and specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof.

18 Claims, No Drawings

METHOD FOR PREPARING 2-[2-(2-CHLOROTHIAZOL-5-YL)-2-OXO-ETHYL]SULFANYL-6-HYDROXY-3-METHYL-5-PHENYL-PYRIMIDIN-4-ONE

CROSS-REFERENCE TO RELATED APPLICATIONS

This is the U.S. national phase of International Application No. PCT/EP2022/051369, filed Jan. 21, 2022, which claims the benefit of European Patent Application No. 21153040.7, filed Jan. 22, 2021.

The present invention relates to a method for preparing 2-[2-(2-chlorothiazol-5-yl)-2-oxo-ethyl]sulfanyl-6-hydroxy-3-methyl-5-phenyl-pyrimidin-4-one or a tautomer thereof, to 2-[2-(2-chlorothiazol-5-yl)-2-oxo-ethyl]sulfanyl-6-hydroxy-3-methyl-5-phenyl-pyrimidin-4-one or a tautomer thereof and to its use as intermediate in the preparation of 2,3-dihydrothiazolo[3,2-a]pyrimidinium compounds, and specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof. The method relates also to 2-hydroxy-4-methyl-5-phenyl-2-sulfanyl-pyrimidinone, to thiolate salts and to tautomers thereof thereof as well as to the use thereof as intermediate(s) in the preparation of 2,3-dihydrothiazolo[3,2-a]pyrimidinium compounds, and specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof.

TECHNICAL BACKGROUND

2-[2-(2-Chlorothiazol-5-yl)-2-oxo-ethyl]sulfanyl-6-hydroxy-3-methyl-5-phenyl-pyrimidin-4-one (or its tautomer) and its precursor 2-hydroxy-4-methyl-5-phenyl-2-sulfanyl-pyrimidinone either in its thiol or thioalte form (or tautomers thereof) have been found to be valuable intermediates in the preparation of 2,3-dihydrothiazolo[3,2-a]pyrimidinium compounds, and more specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof. These pyriminidium compounds have insecticidal properties and are known, for example, from WO 2018/177970 or WO 2014/167084.

The methods thus far known for the preparation of these pyriminidium compounds are cumbersome and not yet satisfactory.

In WO 2018/177970, WO 2018/197541 and WO 2018/202654, non-racemic 2,3-dihydrothiazolo[3,2-a]pyrimidinium compounds are prepared by reaction of a non-racemic 4-heteroaryl-substituted thiazolidin-2-imine with a 2-substituted malonic acid derivative. In WO 2018/177970 and WO 2018/197541, the non-racemic 4-heteroaryl-substituted thiazolidin-2-imine is in turn prepared by catalytic asymmetric hydrogenation of a 1-heteroaryl-substituted ethanimine carrying in 2-position a leaving group. The resulting amine is then reacted with an isothiocyanate to the thiazolidin-2-imine. The reaction sequence is described in WO 2018/197541 as follows:

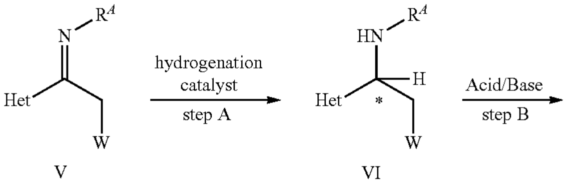

V VI

-continued

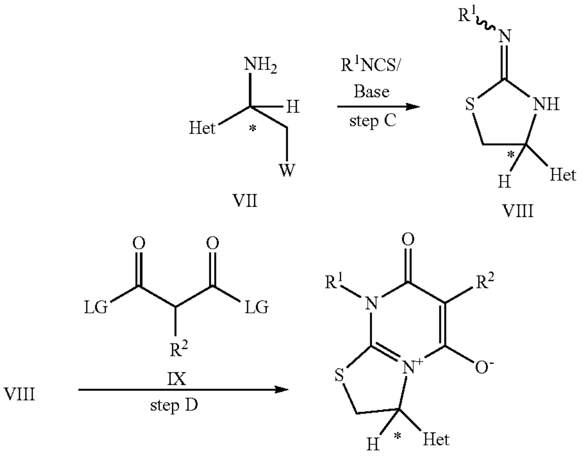

X $R^A$ is a sulfanyl or sulfinyl, phosphoroxy, alkoxy or benzyl group; Het is optionally substituted pyridin-3-yl, thiazol-5-yl or pyrimidin-5-yl, W and LG are leaving groups, $R^1$ is a (cyclo)aliphatic group and $R^2$ is 5- or 6-membered carbo- or heterocyclic ring. In WO 2018/177970 the amine VII is obtained via another reaction path from the corresponding sulfinylimine.

WO 2018/177970 and WO 2018/202654 describe a further access to the non-racemic 4-heteroaryl-substituted thiazolidin-2-imine. This is here prepared starting from a heteroarylmethyl ketone, where the methyl group carries a leaving group, conversion of this leaving group into an alkylcarbonyloxy group, hydrolysis of the latter to a hydroxyl group, reaction of the resulting heteroarylhydroxymethyl ketone with a sulfamoyl halide to a 4-heteroaryl-5H-oxathiazole 2,2-dioxide, submission of the latter to a catalytic asymmetric hydrogenation to yield a non-racemic 4-heteroaryloxathiazolidine 2,2-dioxide and reaction thereof with an isothiocyanate to the thiazolidin-2-imine. The reaction sequence is described in WO 2018/202654 as follows:

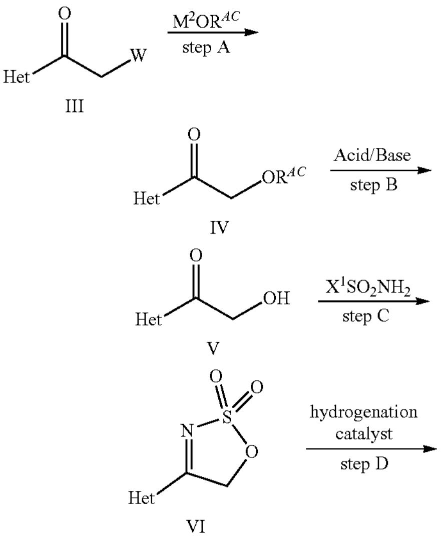

VI

-continued

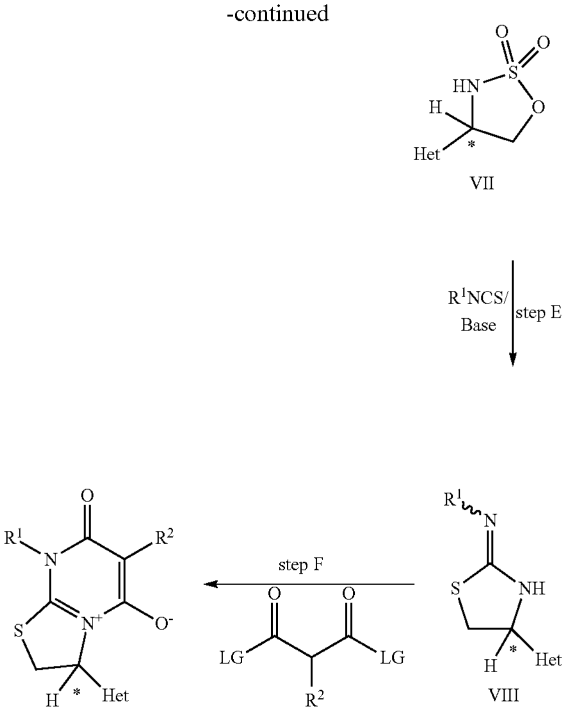

VII VIII IX X

Het is optionally substituted pyridin-3-yl, thiazol-5-yl or pyrimidin-5-yl, W and LG are leaving groups, $M^2$ is Li, Na, K, Al, Ba, Cs, Ca or Mg, $R^{4C}$ is alkylcarbonyl, $X^1$ is halogen, $R^1$ is a (cyclo)aliphatic group and $R^2$ is 5- or 6-membered carbo- or heterocyclic ring.

These methods are however not very economic. Some reagents are expensive, recycling of some of the reagents which are not or not entirely consumed is difficult, the overall yield is not satisfactory and too many reaction steps are involved.

WO 2015/200619 describes the preparation of 2-[2-phenyl-2-oxo-ethyl]sulfanyl-6-hydroxy-3-methyl-5-phenyl-pyrimidin-4-one by reacting N-methylthiourea with dimethyl 2-phenylmalonate to 6-hydroxy-3-methyl-5-phenyl-2-sulfanyl-pyrimidin-4-one and, after isolation, reaction of the latter with 2-bromo-1-phenyl-ethanone. Similar reaction sequences are applied for the synthesis of 2-[2-phenyl-2-oxo-ethyl]sulfanyl-6-hydroxy-3-methyl-5-phenyl-pyrimidin-4-ones carrying substituents on the phenyl ring. This reference does however neither teach nor suggest to prepare heteroaromatic analogs of these compounds nor to modify the halogen atom on the ethanone reactant. Moreover, the yields are rather moderate.

SUMMARY OF THE INVENTION

It was the object of the present invention to provide a more economic process for the preparation of 2-[2-(2-chlorothiazol-5-yl)-2-oxo-ethyl]sulfanyl-6-hydroxy-3-methyl-5-phenyl-pyrimidin-4-one which avoids the drawbacks of the prior art methods.

The problem is solved by a method for preparing 2-[2-(2-chlorothiazol-5-yl)-2-oxo-ethyl]sulfanyl-6-hydroxy-3-methyl-5-phenyl-pyrimidin-4-one of the formula (I):

(I)

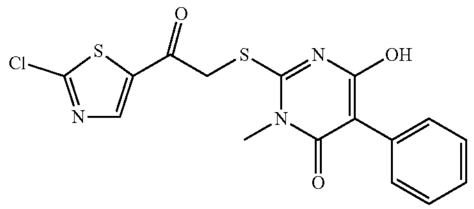

or a tautomer thereof, which method comprises (a) reacting N-methylthiourea of the formula 1 with a 2-phenylmalonate of the formula 2 in the presence of a base

1

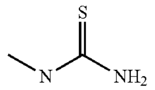

2

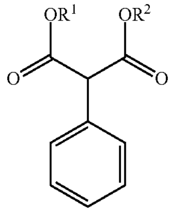

where $R^1$ and $R^2$, independently of each other, are $C_1$-$C_4$-alkyl;

to obtain a reaction mixture containing the pyrimidinone compound of the formula 3

3

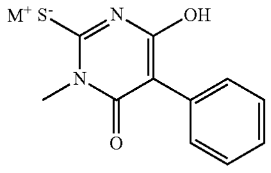

wherein $M^+$ is a cation equivalent;

or a tautomer thereof;

(b) optionally isolating the pyrimidinone compound of the formula 3 (or its tautomer) from the reaction mixture obtained in step (a) either in the form of its salt (i.e. as compound 3 shown above) or in the thiol form (i.e. as compound 3-SH shown below); and (c) reacting either the reaction mixture obtained in step (a) (without isolation of 3 or its tautomer) or the compound obtained in step (b) with the 1-(2-chlorothiazol-5-yl) ethanone of the formula 4

4

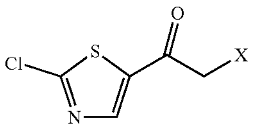

where X is a leaving group, to obtain the compound of the formula (I) or a tautomer thereof.

The invention relates moreover to 2-[2-(2-chlorothiazol-5-yl)-2-oxo-ethyl]sulfanyl-6-hydroxy-3-methyl-5-phenyl-pyrimidin-4-one of the formula (I) depicted above or a tautomer thereof. As said, this compound is a useful intermediate in the preparation of insecticidal 2,3-dihydrothiazolo[3,2-a]pyrimidinium compounds, and more specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof. The invention thus also relates to the use of said compound (or its tautomer) as intermediate in the preparation of 2,3-dihydrothiazolo[3,2-a]pyrimidinium compounds, and specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof.

The invention relates also to 2-hydroxy-4-methyl-5-phenyl-2-sulfanyl-pyrimidinone and to thiolate salts as well as tautomers thereof. The thiolate salts are depicted above as formula 3. These thiol and thiolate compounds are valuable intermediates in the preparation of 2-[2-(2-chlorothiazol-5-yl)-2-oxo-ethyl]sulfanyl-6-hydroxy-3-methyl-5-phenyl-pyrimidin-4-one (I) and thus also in the preparation of downstream insecticidal 2,3-dihydrothiazolo[3,2-a]pyrimidinium compounds, and more specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof. The invention thus also relates to the use of said thiol or thiolate compounds (or tautomers thereof) as intermediates in the preparation of 2-[2-(2-chlorothiazol-5-yl)-2-oxo-ethyl]sulfanyl-6-hydroxy-3-methyl-5-phenyl-pyrimidin-4-one of the formula (I) and to their use as intermediates in the preparation of 2,3-dihydrothiazolo[3,2-a]pyrimidinium compounds, and specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof.

DETAILED DESCRIPTION OF THE INVENTION

Definitions

Halogen as used in terms of the present invention is F, Cl, Br or I.

The term $C_1$-$C_4$-alkyl denotes a saturated linear or branched aliphatic radical with 1 to 4 carbon atoms. Examples are methyl, ethyl, n-propyl, isopropyl, n-butyl, sec-butyl, iso-butyl and tert-butyl.

$C_1$-$C_4$-Alkanols are saturated aliphatic monoalcohols, i.e. $C_1$-$C_4$-alkyl groups, as defined above, in which one of the hydrogen atoms is replaced by a hydroxyl group. Examples are methanol, ethanol, n-propanol, isopropanol, n-butanol, sec-butanol, isobutanol and tert-butanol.

$C_1$-$C_4$-Alkanolates are the salts of $C_1$-$C_4$-alkanols, i.e. in which the hydrogen atom of the hydroxyl group is replaced by a cation equivalent, e.g. a metal cation. Examples are methanolate, ethanolate, n-propanolate, isopropanolate, n-butanolate, sec-butanolate, isobutanolate and tert-butanolate.

Glycols are saturated aliphatic diols. Examples are ethylene glycol, propylene glycol, diethylene glycol and triethylene glycol.

$C_1$-$C_4$-Alkyl acetates are the $C_1$-$C_4$-alkyl esters of acetic acid. Examples are methyl acetate, ethyl acetate, n-propyl acetate, isopropyl acetate, n-butyl acetate, sec-butyl acetate, isobutyl acetate and tert-butyl acetate.

$M^+$ is a cation equivalent. It stands for a metal cation or an ammonium cation (ammonium in this case stands for both the ammonium cation $NH_4^+$ in the proper sense, but also for substituted ammonium cations). In case of cations with double or triple charge, the cation equivalent can be depicted as $(M^{n+})_{1/n}$, where n is the charge number. In compound 3, $M^+$ generally stems from the base used in step (a). Thus, if for example an alkali metal alkanolate, an alkali metal carbonate, an alkali metal hydroxide or an alkali metal phosphate is used as a base in step (a), $M^+$ in compound 3 is generally an alkali metal cation; if an earth alkaline metal carbonate or an earth alkaline metal hydroxide is used as a base, $M^+$ in compound 3 is generally an earth alkaline metal cation $[(M^{2+})_{1/2}]$, and if a non-nucleophilic organic base is used in step (a), $M^+$ in compound 3 is generally the protonated form of this base. $M^+$ may however also stem from bases used in the work-up of the reaction mixture of step (a) in isolation step (b).

The compound (I) can be present as a tautomer thereof or as a mixture of different tautomeric forms. An example for a tautomeric form of the compound of the formula (I) as depicted above is the following formula:

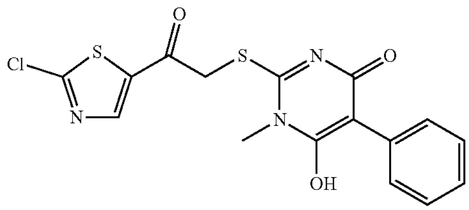 [SMILES: Cn1c(SCC(=O)c2cnc(Cl)s2)nc(=O)c(-c2ccccc2)c1O]

Mixtures of different tautomeric forms are for example mixtures of this tautomer the tautomer depicted above as formula (I).

Also the compound of formula 3 and the neutral thiol form 3-H thereof can be present as tautomers thereof or as mixtures of different tautomeric forms. An example for a tautomeric form of the compound of formula 3 as depicted above is the following formula:

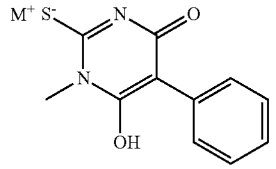

In the thiolate, the negative charge can also be present on the oxygen atom, such as shown in the following:

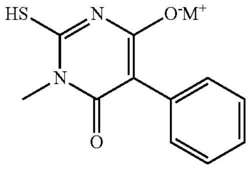

-continued

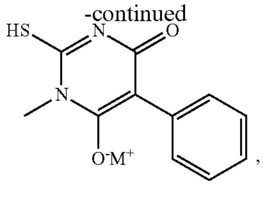

but generally, it is predominately present on the sulfur atom.

Examples for the tautomeric forms of the thiol form 3-H are the following:

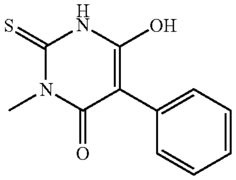

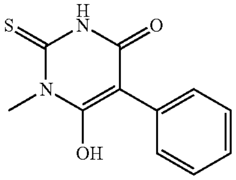

For the sake of simplicity, in the following only compounds (I), 3 and 3-H are mentioned. Nevertheless, all embodiments also relate to their tautomers and mixtures of different tautomeric forms thereof.

EMBODIMENTS (E.x) OF THE INVENTION

General and preferred embodiments E.x are summarized in the following, non-exhaustive list. Further preferred embodiments become apparent from the paragraphs following this list.

E.1. A method for preparing 2-[2-(2-chlorothiazol-5-yl)-2-oxo-ethyl]sulfanyl-6-hydroxy-3-methyl-5-phenyl-pyrimidin-4-one of the formula (I):

(I)

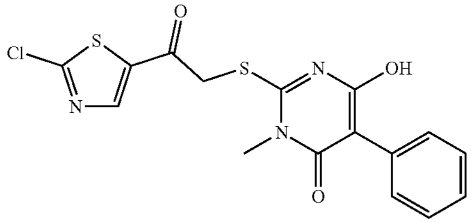

which method comprises (a) reacting N-methylthiourea of the formula 1 with a 2-phenylmalonate of the formula 2 in the presence of a base

1

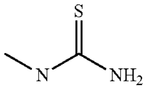

-continued

2

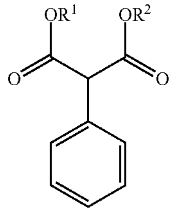

where $R^1$ and $R^2$, independently of each other, are $C_1$-$C_4$-alkyl; to obtain a reaction mixture containing the pyrimidinone compound of the formula 3

3

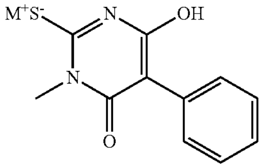

wherein $M^+$ is a cation equivalent;

(b) optionally isolating the pyrimidinone compound of the formula 3 from the reaction mixture obtained in step (a) either in the form of its salt or in the thiol form; and (c) reacting either the reaction mixture obtained in step (a) (without isolation of 3) or the compound obtained in step (b) with the 1-(2-chlorothiazol-5-yl) ethanone of the formula 4

4

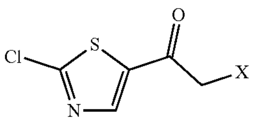

where X is a leaving group, to obtain the compound of the formula (I).

E.2. The method according to embodiment E.1, where $R^1$ and $R^2$, independently of each other, are methyl or ethyl.

E.3. The method according to embodiment E.2, where $R^1$ and $R^2$ are both methyl or are both ethyl.

E.4. The method according to any of the preceding embodiments, where the base used in step (a) is selected from the group consisting of alkali metal $C_1$-$C_4$-alkanolates, alkali metal carbonates, earth alkaline metal carbonates, alkali metal hydroxides, earth alkaline metal hydroxides, alkali metal phosphates, non-nucleophilic organic bases and mixtures thereof.

E.5. The method according to embodiment E.4, where the base used in step (a) is selected from the group consisting of alkali metal $C_1$-$C_4$-alkanolates, alkali metal carbonates and mixtures thereof; and in particular from alkali metal $C_1$-$C_4$-alkanolates.

E.6. The method according to embodiment E.5, where the base used in step (a) is selected from the group consisting of sodium methanolate, sodium ethanolate, sodium isopropanolate, sodium tert-butanolate, potassium methanolate, potassium ethanolate, potassium tert-butanolate, lithium methanolate, and mixtures thereof.

E.7. The method according to embodiment E.6, where the base used in step (a) is selected from the group consisting of sodium methanolate, potassium methanolate, sodium ethanolate, potassium ethanolate and mixtures thereof; and is specifically sodium methanolate or potassium methanolate.

E.8. The method according to any of the preceding embodiments, where in step (a) the 2-phenylmalonate 2 is used in an amount of from 0.8 to 2.0 mol per mol of N-methylthiourea 1.

E.9. The method according to embodiment E.8, where in step (a) the 2-phenylmalonate 2 is used in an amount of 1.0 to 1.3 mol per mol of N-methylthiourea 1.

E.10. The method according to any of the preceding embodiments, where in step (a) the base is used in an amount of from 0.8 to 1.5 mol per mol of N-methylthiourea 1

E.11. The method according to embodiment E.10, where in step (a) the base is used in an amount of 1.0 to 1.5 mol per mol of N-methylthiourea 1.

E.12. The method according to any of the preceding embodiments, where the reaction in step (a) and (c) is carried out in a solvent.

E.13. The method according to embodiment E.12, where the solvent is selected from the group consisting of polar protic solvents, polar aprotic solvents, $C_1$-$C_4$-alkyl acetates, dialkyl ethers, aromatic solvents, heterocyclic solvents and mixtures thereof.

E.14. The method according to embodiment E.13, where the solvent is selected from the group consisting of $C_1$-$C_4$-alkanols, glycols, tetrahydrofuran, 2-methyltetrahydrofuran, the dioxanes, dimethylformamide, dimethylacetamide, dimethylsulfoxide, $C_1$-$C_4$-alkyl acetates, di-n-propyl ether, di-n-butyl ether, methyl-tert-butyl ether, acetonitrile, benzene, toluene, the xylenes, chlorobenzene, dichlorobenzene, N-methylpyrrolidone and mixtures thereof.

E.15. The method according to embodiment E.14, where the solvent is selected from the group consisting of methanol, ethanol, n-propanol, isopropanol, isobutanol, tert-butanol, tetrahydrofuran, 2-methyltetrahydrofuran, 1,4-dioxane, dimethylformamide, dimethylacetamide, toluene, chlorobenzene, N-methylpyrrolidone and mixtures thereof; and preferably from the group consisting of methanol, ethanol, dimethylacetamide, toluene, chlorobenzene and mixtures thereof.

E.16. The method according to embodiment E.15, where step (a) is carried out in a solvent selected from the group consisting of methanol, ethanol, a mixture of methanol and ethanol, and a mixture of methanol and/or ethanol with at least one further solvent which is selected from the group consisting of dimethylacetamide, toluene and chlorobenzene, and step (c) is carried out in a solvent selected from the group consisting of methanol, ethanol, dimethylacetamide, toluene, chlorobenzene and mixtures of at least two of the aforementioned solvents.

E.17. The method according to any of the preceding embodiments, where step (a) is carried out at a temperature of from 10° C. to the reflux temperature of the reaction mixture.

E.18. The method according to embodiment E.17, where step (a) is carried out at a temperature of from 20° C. to the reflux temperature of the reaction mixture.

E.19. The method according to embodiment E.18, where step (a) is carried out at a temperature of from 45 to 75° C.

E.20. The method according to any of the preceding embodiments, where the reaction time of step (a) is from 1 h to 60 h.

E.21. The method according to embodiment E.20, where the reaction time of step (a) is from 4 h to 18 h.

E.22. The method according to any of the preceding embodiments, where in step (a) either (a.1) the 2-phenylmalonate 2 is added to an optionally heated solution of methylthiourea 1 and the base in a solvent; or (a.2) the base, optionally in a solvent, is added to an optionally heated mixture of methylthiourea 1, the 2-phenylmalonate 2 and optionally a solvent; or (a.3) a mixture of methylthiourea 1, the 2-phenylmalonate 2, the base and optionally a solvent is prepared and reacted, optionally under heating; or (a.4) methylthiourea 1, optionally in a solvent, is added to an optionally heated mixture of the 2-phenylmalonate 2, the base and optionally a solvent;

where the proceeding according to (a.1) or (a.2) is preferred.

E.23. The method according to any of the preceding embodiments, where in step (c) the reaction mixture obtained in step (a) is reacted with the compound of formula 4.

E.24. The method according to any of the preceding embodiments, where X in the compound of formula 4 is selected the group consisting of halogen, triflate, mesylate, tosylate and nonaflate.

E.25. The method according to embodiment 24, where X in the compound of formula 4 is selected the group consisting of Cl, Br and I.

E.26. The method according to embodiment 25, where X in the compound of formula 4 is selected the group consisting of Cl and Br.

E.27. The method according to embodiment 26, where X in the compound of formula 4 is Cl.

E.28. The method according to any of the preceding embodiments, where in step (c) the 1-(2-chlorothiazol-5-yl) ethanone 4 is used in an amount of from 0.8 to 1.5 mol per mol of N-methylthiourea 1 used in step (a).

E.29. The method according to embodiment E.28, where in step (c) the 1-(2-chlorothiazol-5-yl) ethanone 4 is used in an amount of from 1.0 to 1.5 mol per mol of N-methylthiourea 1 used in step (a).

E.30. The method according to any of the preceding embodiments, where step (c) is carried out at a temperature of from −20 to 120° C.

E.31. The method according to embodiment E.30, where step (c) is carried out at a temperature of from 25 to 80° C.

E.32. The method according to embodiment E.31, where step (c) is carried out at a temperature of from 40 to 80° C.

E.33. The method according to any of the preceding embodiments, where step (c) is carried out in the presence of an additive selected from the group consisting of alkali metal bromides, alkali metal iodides, ammonium bromides, ammonium iodides and mixtures thereof.

E.34. The method according to embodiment E.33, where the additive is selected from the group consisting of NaBr, KBr, NaI, KI, tetrabutylammonium bromide and mixtures thereof.

E.35. The method according to any of embodiments E.33 or E.34, where the additive is used in such an amount that the molar ratio of additive and the 1-(2-chlorothiazol-5-yl) ethanone 4 is in the range of preferably from 1:100 to 10:1, more preferably from 1:20 to 2:1, in particular from 1:2 to 2:1.

E.36. The method according to any of the preceding embodiments, where in step (c) either (c.1) the reaction mixture obtained in step (a) or the product obtained in step (b) is added to a solution of the 1-(2-chlorothiazol-5-yl)ethanone 4; or (c.2) a solution or a melt of the 1-(2-chlorothiazol-5-yl) ethanone 4 is added to the reaction mixture obtained in step (a) or to a solution of the product obtained in step (b).

E.37. The method according to embodiment E.36, where step (c) is carried out according to proceeding (c.2).

E.38. The method according to any of embodiments E.36 or E.37, where in case of the proceeding according to (c.2), the solution or the melt of the 1-(2-chlorothiazol-5-yl) ethanone 4 is added within 15 min to 12 h to the reaction mixture obtained in step (a) or to the solution of the product obtained in step (b).

E.39. The method according to embodiment E.38, where the solution or the melt of the 1-(2-chlorothiazol-5-yl) ethanone 4 is added within 0.5 h to 6 h to the reaction mixture obtained in step (a) or to the solution of the product obtained in step (b).

E.40. The method according to any of the preceding embodiments, where after mixing the complete amount of the reaction mixture obtained in step (a) or the product obtained in step (b) and the 1-(2-chlorothiazol-5-yl)ethanone 4, the reaction mixture is reacted for 0 to 60 h.

E.41. The method according to embodiment E.40, where the reaction mixture is reacted for 1 h to 40 h.

E.42. The method according to embodiment E.41, where the reaction mixture is reacted for 1 to 18 h.

E.43. 2-[2-(2-Chlorothiazol-5-yl)-2-oxo-ethyl]sulfanyl-6-hydroxy-3-methyl-5-phenyl-pyrimidin-4-one of the formula (I):

(I)

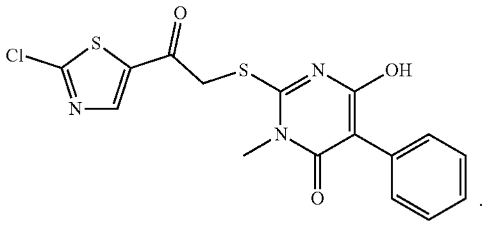

E.44. Pyrimidinone compound of the formula 3

3

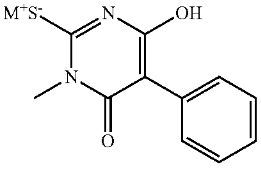

wherein $M^+$ is a cation equivalent, preferably an alkali metal cation, in particular $Na^+$ or $K^+$;

or the corresponding thiol (i.e. —SH instead of —$S^-M^+$.

The reaction sequence of the method of the invention can be depicted as follows:

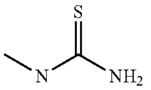

1

+

-continued

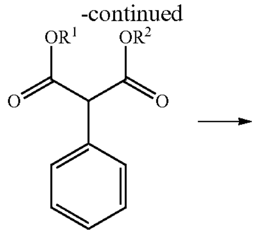

2

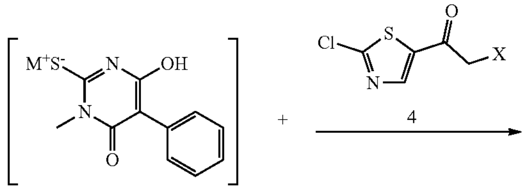

3

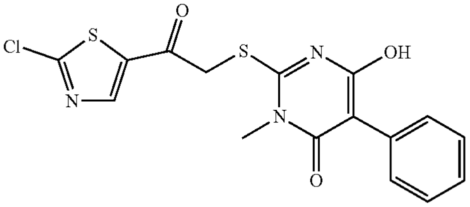

(I)

The brackets around the compound 3 indicate that the reaction can be carried out with or without isolating compound 3.

In the 2-phenylmalonate of the formula 2, $R^1$ and $R^2$, independently of each other, are preferably methyl or ethyl. In particular $R^1$ and $R^2$ are both methyl or are both ethyl.

The base used in step (a) is preferably selected from the group consisting of alkali metal $C_1$-$C_4$-alkanolates, alkali metal carbonates, earth alkaline metal carbonates, alkali metal hydroxides, earth alkaline metal hydroxides, alkali metal phosphates, non-nucleophilic organic bases and mixtures thereof.

Alkali metal cations suitable as counter cations in the alkanolates, carbonates, hydroxides and phosphates are for example $Li^+$, $Na^+$, $K^+$and $Cs^+$. Among these, preference is given to $Na^+$ and $K^+$. Earth alkaline metals suitable as counter cations in the alkanolates, carbonates and hydroxides are for example $Mg^{2+}$ and $Ca^{2+}$.

Examples of suitable alkali metal $C_1$-$C_4$-alkanolates are lithium, sodium, potassium, or cesium methanolate, lithium, sodium, potassium, or cesium ethanolate, lithium, sodium, potassium, or cesium n-propanolate, lithium, sodium, potassium, or cesium isopropanolate, lithium, sodium, potassium, or cesium n-butanolate, lithium, sodium, potassium, or cesium sec-butanolate, lithium, sodium, potassium, or cesium isobutanolate and lithium, sodium, potassium, or cesium tert-butanolate.

Examples for suitable alkali metal carbonates are lithium, sodium, potassium, or cesium carbonate.

Examples for suitable earth alkaline metal carbonates are magnesium and calcium carbonate.

Examples of suitable alkali metal phosphates are lithium, sodium, potassium, or cesium phosphate.

Non-nucleophilic organic bases are generally sterically hindered organic bases, such that protons can attach to the basic center, but alkylation and complexation is inhibited.

Examples are 1,8-diazabicyclo[5.4.0]undec-7-ene (DBU) and 1,5-diazabicyclo[4.3.0]-non-5-ene (DBN).

The base used in step (a) is preferably selected from the group consisting of alkali metal $C_1$-$C_4$-alkanolates, such as those listed above, alkali metal carbonates, such as those listed above, and mixtures thereof. More preferably, the base is selected from alkali metal $C_1$-$C_4$-alkanolates.

In particular, the base used in step (a) is selected from the group consisting of sodium methanolate, sodium ethanolate, sodium isopropanolate, sodium tert-butanolate, potassium methanolate, potassium ethanolate, potassium tert-butanolate, lithium methanolate, and mixtures thereof; more particularly from the group consisting of sodium methanolate, potassium methanolate, sodium ethanolate, potassium ethanolate and mixtures thereof; and is specifically sodium methanolate or potassium methanolate.

The 2-phenylmalonate 2 is used in step (a) in an amount of preferably from 0.8 to 2.0 mol per mol of N-methylthiourea 1; in particular in an amount of 1.0 to 1.3 mol per mol of N-methylthiourea 1.

The base is used in step (a) in an amount of preferably from 0.8 to 1.5 mol per mol of N-methylthiourea 1; in particular in an amount of 1.0 to 1.5 mol per mol of N-methylthiourea 1.

The reactions in steps (a) and (c) are preferably carried out in a solvent.

The solvent is preferably selected from the group consisting of polar protic solvents, polar aprotic solvents, $C_1$-$C_4$-alkyl acetates, dialkyl ethers, aromatic solvents, heterocyclic solvents and mixtures thereof. Polar protic solvents are for example alkanols, such as methanol, ethanol, n-propanol, isopropanol, n-butanol, sec-butanol, isobutanol and tert-butanol, and glycols, such as ethylene glycol, propylene glycol, diethylene glycol and triethylene glycol. Polar aprotic solvents are for example cyclic ethers, such as tetrahydrofuran, 2-methyltetrahydrofuran and the dioxanes (i.e. 1,3- and 1,4-dioxane), dimethylformamide, dimethylacetamide, dimethylsulfoxide or acetonitrile. $C_1$-$C_4$-alkyl acetates are for example methyl acetate, ethyl acetate, n-propyl acetate, isopropyl acetate, n-butyl acetate, sec-butyl acetate, isobutyl acetate and tert-butyl acetate. Dialkyl ethers are for example diethyl ether, di-n-propyl ether, di-n-butyl ether or methyl-tert-butyl ether. Aromatic solvents are for example benzene, toluene, the xylenes, chlorobenzene or dichlorobenzene. A suitable heterocyclic solvent is for example methylpyrrolidone.

More preferably, the solvent is selected from the group consisting of $C_1$-$C_4$-alkanols, glycols, tetrahydrofuran, 2-methyltetrahydrofuran, the dioxanes, dimethylformamide, dimethylacetamide, dimethylsulfoxide, $C_1$-$C_4$-alkyl acetates, di-n-propyl ether, di-n-butyl ether, methyl-tert-butyl ether, acetonitrile, benzene, toluene, the xylenes, chlorobenzene, dichlorobenzene, N-methylpyrrolidone and mixtures thereof. More preferably, the solvent is selected from the group consisting of methanol, ethanol, n-propanol, isopropanol, isobutanol, tert-butanol, tetrahydrofuran, 2-methyltetrahydrofuran, 1,4-dioxane, dimethylformamide, dimethylacetamide, toluene, chlorobenzene, N-methylpyrrolidone and mixtures thereof; and in particular from the group consisting of methanol, ethanol, dimethylacetamide, toluene, chlorobenzene and mixtures thereof.

In a specific embodiment, step (a) is carried out in a solvent selected from the group consisting of methanol, ethanol, a mixture of methanol and ethanol, and a mixture of methanol and/or ethanol with at least one further solvent which is selected from the group consisting of dimethylacetamide, toluene and chlorobenzene, and step (c) is carried out in a solvent selected from the group consisting of methanol, ethanol, dimethylacetamide, toluene, chlorobenzene and mixtures of at least two of the aforementioned solvents. More specifically, step (a) is carried out in a solvent selected from the group consisting of methanol, ethanol and a mixture of methanol and ethanol, and step (c) is carried out in a solvent selected from the group consisting of methanol, ethanol, dimethylacetamide, toluene, chlorobenzene and mixtures of at least two of the aforementioned solvents.

Step (a) is preferably carried out at a temperature of from 10° C. to the reflux temperature of the reaction mixture, more preferably from 20° C. to the reflux temperature of the reaction mixture, in particular from 45 to 75° C.

The reaction time of step (a) depends on various factors, such as the reaction temperature, the concentration of the reactants in the reaction mixture and the like. Typically, it is in the range of from about 1 h to 60 h, preferably from 4 h to 18 h.

The order of addition of the reactants, solvent, if any, and base in step (a) is not critical. For instance, (a.1) the 2-phenylmalonate 2 can be added to an optionally heated solution of methylthiourea 1 and the base in a solvent; or (a.2) the base, optionally in a solvent, can be added to an optionally heated mixture of methylthiourea 1, the 2-phenylmalonate 2 and optionally a solvent; or (a.3) a mixture of all components, i.e. of methylthiourea 1, the 2-phenylmalonate 2, the base and optionally a solvent, is prepared and reacted, optionally under heating; or (a.4) methylthiourea 1, optionally in a solvent, can be added to an optionally heated mixture of the 2-phenylmalonate 2, the base and optionally a solvent.

The proceeding according to (a.1) or (a.2) is however preferred.

In optional step (b), the pyrimidinone compound of the formula 3 can be isolated from the reaction mixture obtained in step (a) by usual methods, e.g. by partially or completely removing the solvent, optionally under reduced pressure, or by adding a solvent to the reaction mixture in which 3 has no or low solubility, optionally after concentrating the reaction mixture. Suitable solvents are for example aliphatic and cycloaliphatic hydrocarbons, such as pentane, hexane, heptane, cyclohexane and the like, acyclic ethers, such as diethyl ether, di-n-propyl ether, di-n-butyl ether and methyl tert-butyl ether, aromatic solvents, such as benzene, toluene, the xylenes, chlorobenzene or dichlorobenzene, and halogenated alkanes, such as dichloromethane, trichloromethane and dichloroethane. Depending on the reaction conditions of step (a), especially the reaction temperature and the solvent used, compound 3 can also precipitate just upon cooling the reaction mixture. The precipitate can then be isolated by usual means, such as filtration. Further purification of the isolated product, if desired, can be carried out by usual methods, such as trituration or recrystallization. Generally, the product can however be used in step (c) without further purification.

To obtain the corresponding thiol, which is a compound of the formula 3-SH

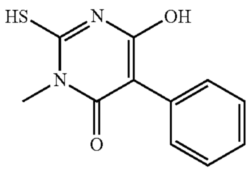

3-SH compound 3 can be acidified, which is generally carried out in solution. Acidification can principally also be carried out before isolating the compound 3 from the reaction mixture obtained in step (a). Suitable acids can be inorganic (e.g. HCl, $H_2SO_4$, $H_3PO_4$ etc.) or organic (e.g. acetic acid, trifluoroacetic acid etc).

In step (c), either the reaction mixture obtained in step (a) (without isolation of 3) or the compound 3 obtained in step (b) or the corresponding thiol 3-SH is reacted with the compound of formula 4. If the thiol 3-SH is used as starting material, it is expedient to convert it first into the thiolate 3 or to carry out step (c) in the presence of a base. Suitable bases are those listed above in context with step (a).

Preference is however given to react the reaction mixture obtained in step (a) with 4, i.e. to skip the isolation step (b).

In the 1-(2-chlorothiazol-5-yl)ethanone 4 X is a leaving group. Suitable leaving groups are for example halogen atoms, in particular Cl, Br or I, and sulfonates, such as triflate, mesylate, tosylate or nonaflate. Preference is given to X being a halogen atom, preferably Cl, Br or I, more preferably Cl or Br and in particular Cl.

In step (c), the 1-(2-chlorothiazol-5-yl)ethanone 4 is used in an amount of preferably from 0.8 to 1.5 mol per mol of N-methylthiourea 1; in particular in an amount of 1.0 to 1.5 mol per mol of N-methylthiourea 1 used in step (a).

If in step (c) the compound 3 obtained in step (b) or the corresponding thiol 3-SH is reacted with the compound of formula 4, the 1-(2-chlorothiazol-5-yl)ethanone 4 is used in an amount of preferably from 0.8 to 1.5 mol per mol of N-methylthiourea 1; in particular in an amount of 1.0 to 1.5 mol per mol of compound 3 or 3-SH.

Step (c) is carried out at a temperature of preferably from −20 to 120° C., more preferably from 25 to 80° C., in particular from 40 to 80° C.

In a specific embodiment, step (c) is carried out in the presence of an additive (especially if X is Cl; see the following explanation). Such additives are to ease the nucleophilic attack of the thiol or thiolate group in 3 on the X-substituted aliphatic carbon atom in 4. The effect of such additives is of particular relevance if X is Cl. Suitable additives are selected from the group consisting of alkali metal bromides, alkali metal iodides, ammonium bromides, ammonium iodides and mixtures thereof, where the additive is preferably selected from the group consisting of NaBr, KBr, NaI, KI, tetrabutylammonium bromide and mixtures thereof. Without wishing to be bound by theory, for the case that X is Cl, it is supposed that the bromide or iodide substitutes a part of the $CH_2$-bound Cl in 4. One aspect is that bromides and iodides are generally more reactive than chlorides, which accelerates the reaction. Another aspect is that C—Br and C—I are softer reaction centers than C—Cl. According to the HSAB concept, the reaction with the soft thiol or thiolate nucleophile 3 is thus favoured.

The additive is used in such an amount that the molar ratio of additive and the 1-(2-chlorothiazol-5-yl) ethanone 4 is preferably in the range of from 1:100 to 10:1, more preferably from 1:20 to 2:1, in particular from 1:2 to 2:1.

The order of addition of the reactants in step (c) is not critical. For instance, (c.1) the reaction mixture obtained in step (a) or the product obtained in step (b) can be added to a solution of the 1-(2-chlorothiazol-5-ypethanone 4; or (c.2) a solution or a melt of the 1-(2-chlorothiazol-5-yl) ethanone 4 can be added to the reaction mixture obtained in step (a) or to the product obtained in step (b).

In (c.1), the product obtained in step (b) can be added as such (it is generally obtained as a solid) or in solution or dispersion. If the product is added in dissolved or dispersed form, the solvent used for this purpose is suitably one in which step (c) is to be carried out.

If in (c.2) a solution or a melt of the 1-(2-chlorothiazol-5-yl)ethanone 4 is added to the product obtained in step (b), the product is expediently present in dissolved or dispersed form; the solvent used for this purpose being again suitably one in which step (c) is to be carried out.

Preference is given to the proceeding according (c.2).

In case that step (c) is carried out according to the proceeding of (c.2), the solution or the melt of the 1-(2-chlorothiazol-5-yl)ethanone 4 is preferably added within 15 min to 12 h, in particular within 0.5 h to 6 h, to the reaction mixture obtained in step (a) or to the product obtained in step (b)—suitably to its solution or dispersion.

After mixing the complete amount of the reaction mixture obtained in step (a) or the product obtained in step (b) and the 1-(2-chlorothiazol-5-yl)ethanone 4, the reaction mixture is preferably reacted for 0 to 60 h, more preferably for 1 h to 40 h, in particular 1 to 18 h. Reaction for "0 h" in this context means that after complete addition of the reactants, the reaction can be sufficiently complete to continue with the isolation of the desired compound (I). This can for example be the case if the addition of the reactants has lasted rather long or if it is intended to recycle the non-reacted starting material.

The compound (I) can be isolated from the reaction mixture by known means. Given that it has low solubility at room temperature in most of the solvents which are preferably used in step (c), especially in the more polar ones, it can for example be isolated by precipitation. Partially, the product precipitates yet during the reaction, especially if the reaction is carried out at rather low temperatures, e.g. below 30° C. and if the reaction mixture is not too diluted. Precipitation can be furthered by lowering the temperature, by removing a part of the solvent and/or by adding water to the reaction mixture.

The precipitate can be isolated by usual methods, such as filtration, centrifugation, sedimentation and removal of the supernatant etc., where filtration is preferred. The filter cake can be further purified by washing with suitable solvents, such as methanol, ethanol, isopropanol, toluene, dimethylacetamide, water, basic aqueous solutions, such as aqueous $NaHCO_3$, $Na_2CO_3$, $K_2CO_3$, NaOH, KOH or $NH_3$ solutions, or mixtures thereof. Washing with water or aqueous solutions can be carried out over a wide temperature range, such as 0-100° C., preferably from 25-80° C. Washing with organic solvents can also be carried out over a wide temperature range, such as 0-100° C., but is preferably done with solvents having a temperature of from 0 to 35° C., in particular from 10 to 25° C.

Compounds 1 and 2 are commercially available or can be prepared by standard methods.

Compound 4 can be prepared, for example, as described in WO 2018/197541 or WO 2018/202654 by reaction of 2-chlorothiazole with a Grignard reagent to the corresponding chloro-(2-chlorothiazol-5-yl) magnesium species and reaction thereof with 2-halogeno-N-methoxy-N-metyl-acetamide. Alternatively, the compound 4 can be prepared from thiourea according the method described by T. Chalopin et al. in Org. Biomol. Chem., 2016, 14, 3913-3925.

The present method leads to the compound (I) in high yields and purities and requires just a few steps starting from readily available starting materials. Contrary to the method described in WO 2015/200619 it does not require the use of organic bromine compounds, which are rather expensive, as starting material. It is of course nevertheless possible to use the bromine or even iodine compounds, i.e. compounds 4 where X is Br or I; but given that compounds 4 wherein X is another leaving group and especially Cl lead to excellent yields, the use of compounds 4 where X is Br or I is not imperative, but just an alternative option.

The invention relates moreover to 2-[2-(2-chlorothiazol-5-yl)-2-oxo-ethyl]sulfanyl-6-hydroxy-3-methyl-5-phenyl-pyrimidin-4-one of the formula (I) or a tautomer thereof or a mixture of tautomeric forms thereof, which is a valuable intermediate in the preparation of insecticidal 2,3-dihydrothiazolo[3,2-a]pyrimidinium compounds, and more specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof. The invention relates also to the use of the compound (I) or a tautomer thereof or a mixture of tautomeric forms thereof as intermediate in the preparation of 2,3-dihydrothiazolo[3,2-a]pyrimidinium compounds, and specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof.

The compound (I) (or a tautomer thereof or a mixture of tautomeric forms thereof) can be converted in just two further steps into 3-(2-chlorothiazol-5-yl)-8-methyl-7-oxo-6-phenyl-2,3-dihydrothiazolo[3,2-a]pyrimidin-4-ium-5-olate, and especially into enantiomerically enriched forms thereof. For obtaining enantiomerically enriched forms, the compound (I) (or a tautomer thereof or a mixture of tautomeric forms thereof) is subjected to an asymmetric hydrogenation of the keto group to the respective alcohol in an enantiomerically enriched form, and said alcohol is subjected to an internal cyclization by a nucleophilic attack of the unsubstituted nitrogen atom of the pyrimidine ring on the carbon atom carrying the aliphatic OH group. As a matter of course, for obtaining the racemic form of 3-(2-chlorothiazol-5-yl)-8-methyl-7-oxo-6-phenyl-2,3-dihydrothiazolo[3,2-a]pyrimidin-4-ium-5-olate, hydrogenation of (I) (or a tautomer thereof or a mixture of tautomeric forms thereof) can be carried out under non-chiral conditions. The reaction sequence can be depicted as follows:

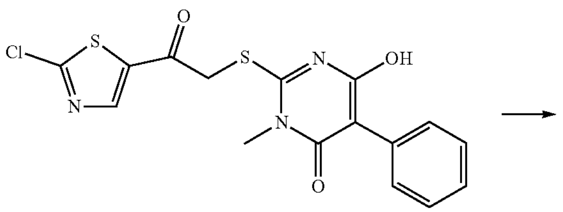

(I)

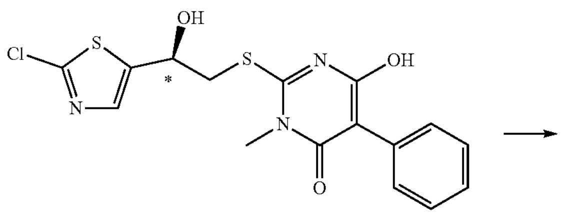

-continued

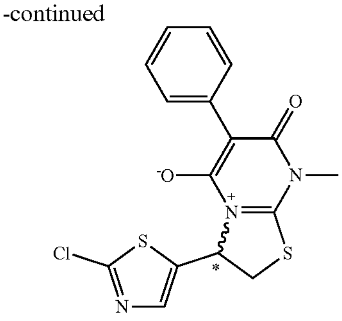

These reactions are described in more detail in EP applications no. 21153034.0, 21153036.5 and 21153038.1.

The invention relates also to pyrimidinone compounds of the formula 3 as defined above or a tautomer thereof or a mixture of tautomeric forms thereof and to the corresponding thiol 3-SH or a tautomer thereof or a mixture of tautomeric forms thereof; and to the use thereof as intermediate in the preparation of 2-[2-(2-chlorothiazol-5-yl)-2-oxo-ethyl]sulfanyl-6-hydroxy-3-methyl-5-phenyl-pyrimidin-4-one of the formula (I) or a tautomer thereof or a mixture of tautomeric forms thereof as well as the use thereof as intermediate in the preparation of 2,3-dihydrothiazolo[3,2-a]pyrimidinium compounds, and specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof.

The thiol of 3 has the following formula 3-SH:

3-SH

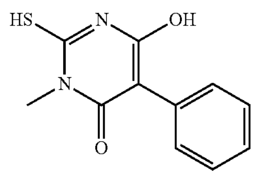

As is understood from the above, the compound 3 or 3-SH (or a tautomer thereof or a mixture of tautomeric forms thereof) can be converted in three further steps into 3-(2-chlorothiazol-5-yl)-8-methyl-7-oxo-6-phenyl-2,3-dihydrothiazolo[3,2-a]pyrimidin-4-ium-5-olate, and especially into enantiomerically enriched forms thereof; the first step being the reaction of 3 or 3-SH with 4 to the compound (I) (or to a tautomer thereof or a mixture of tautomeric forms thereof).

The present invention is further illustrated in the following examples.

EXAMPLES

Methods

The compounds can be characterized by coupled High Performance Liquid Chromatography/mass spectrometry (HPLC/MS), by NMR or by melting points.

HPLC method: Agilent Eclipse XDB-C18, 150 mm×4.6 mm ID×5 μm

Gradient A=0.5% $H_2SO_4$ in water, B=acetonitrile.

Flow=1.1 mL/min

Column oven temperature=30° C.

Gradient program=20% B-100% B—15 min

Run Time=15 min

LCMS method 1: C18 Column (50 mm×2.1 mm×1.7 μm)

Gradient A=0.1% TFA in water, B=acetonitrile

Flow=0.8 mL/min to 1.0 mL/min in 1.5 min

Column oven temperature=60° C.

Gradient program=10% B to 100% B in 15 min, hold for 1 min 100% B, 1 min—10% B

Run time: 1.75 min $^1$H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplet, q=quartet, t=triplet, d=doublet and s=singlet.

Abbreviations used are: h for hour(s), min for minute(s), rt for retention time, r.t. for room temperature (20-25° C.), TFA for trifluoroacetic acid.

Example 1: Preparation of 2-[2-(2-chlorothiazol-5-yl)-2-oxo-ethyl]sulfanyl-6-hydroxy-3-methyl-5-phenyl-pyrimidin-4-one In a 20 L jacketed reactor, a solution of N-methylthiourea (778 g, 8.38 mol) and $NaOCH_3$ (1584 g, 8.79 mol, 30 wt % solution in methanol) and methanol (384 g, 12 mol) under $N_2$ was warmed to an internal temperature of 65° C. Then diethyl 2-phenylmalonate (2121 g, 8.79 mol) was dosed over 30 min, and the pump was washed with methanol (384 g, 12 mol). The reaction was then stirred for 4 h at an internal temperature of 65° C., and then for 18 h at 50° C. Over this time a suspension formed. Then a solution of 2-chloro-1-(2-chlorothiazol-5-yl)ethanone (1859 g, 9.00 mol) in ethanol (8.050 g, 175 mol) was dosed over 30 min. The reaction was stirred 75 min at 50° C., and a large precipitation of solid occurred. At this point ethanol (2.300 g, 50 mol) was added, and the stirring speed was increased. The reaction was stirred at 50° C. a further 36 h and then reaction was then cooled to 20° C. over 16 h. The formed solid was then isolated via filtration in three 4 L fritted funnels. Each filtercake was washed with 500 mL of ethanol. The filtercake was then returned to the 20 L reactor and slurried with 15 L of water at 75° C. for 1 h. The slurry was then filtered in two 4 L fritted funnels, and each filtercake washed three times with 500 mL of room temperature water, and then dried at 80° C. and 5 mbar in a vacuum drying oven. After drying 3040 g (91%) of the title compound in form of a brown solid in 99 wt % purity were isolated.

$^1$H NMR (400 MHz, DMSO-d6): δ=8.75 (s, 1H), 7.15-7.45 (m, 5H), 4.9 (s, 2H), 3.46 (s, 3H).

Example 2: Preparation of 2-[2-(2-chlorothiazol-5-yl)-2-oxo-ethyl]sulfanyl-6-hydroxy-3-methyl-5-phenyl-pyrimidin-4-one In a 20 L jacketed reactor, a solution of N-methylthiourea (778 g, 8.38 mol) and $NaOCH_3$ (1584 g, 8.79 mol, 30 wt % solution in methanol) and methanol (384 g, 12 mol) under N2 was warmed to an internal temperature of 65° C. Then diethyl 2-phenylmalonate (2121 g, 8.79 mol) was dosed over 30 min, and the pump was washed with methanol (384 g, 12 mol). The reaction was then stirred for 4 h at an internal temperature of 65° C., and then for 18 h at 50° C. Over this time a suspension formed. Then a solution of 2-chloro-1-(2-chlorothiazol-5-yl)ethanone (1859 g, 9.00 mol) in ethanol (10,000 g, 217 mol) was dosed over 6 h. The pump was cleaned with ethanol (350 g, 7.61 mol). The reaction was stirred at 50° C. for 36 h after addition was complete, and the reaction was then cooled to 20° C. over 16 h. Two hours after the addition of 2-chloro-1-(2-chlorothiazole-5-yl) ethanone was started, a beige suspension formed in the reactor. The formed solid was isolated via filtration in three 4 L fritted funnels. Each filtercake was washed with 500 mL of ethanol three times. he filtercake was then returned to the 20 L reactor and slurried with 15 L of water at 75° C. for 1 h. The slurry was then filtered in two 4 L fritted funnels, and each filtercake washed three times with 500 mL of room temperature water, and then dried at 80° C. and 5 mbar in a vacuum drying oven. After drying 3055 g (91%) of the title compound in form of a light brown solid in 99 wt % purity is isolated.

Example 3: Preparation of 2-[2-(2-chlorothiazol-5-yl)-2-oxo-ethyl]sulfanyl-6-hydroxy-3-methyl-5-phenyl-pyrimidin-4-one In a 500 mL round bottom flask equipped with an overhead stirrer and reflux condenser a solution of N-methylthiourea (15.56 g, 167.4 mmol) and diethyl 2-phenylmalonate (42.38 g, 175.8 mmol) under $N_2$ at 35° C. was prepared. Then to this solution was dosed $NaOCH_3$ (31.56 g, 175.8 mol, 30 wt % solution in methanol) over 2 h, during which a suspension formed. The reaction was stirred a further 24 h at 35° C., and then a solution of 2-chloro-1-(2-chlorothiazol-5-yl)ethanone (35.8 g, 180.0 mmol) in ethanol (204 g, 444 mol) was dosed over 2 h. The reaction was stirred at 50° C. for 36 h after addition was complete, and then cooled to 20° C. The formed solid was isolated via filtration in a fritted funnel. The filtercake was washed with 100 mL of ethanol three times, until the filtrate ran colorless. The filtercake was then returned to the reactor and slurried with 400 g of water at 70° C. for 1 h. The slurry was filtered a fritted funnel, and the filtercake washed three times with 40 mL of room temperature water, and then dried at 80° C. and 5 mbar in a vacuum drying oven to afford 59.1 g (90% yield) of the title compound in form of a cream colored solid.

Example 4: Preparation of 2-[2-(2-chlorothiazol-5-yl)-2-oxo-ethyl]sulfanyl-6-hydroxy-3-methyl-5-phenyl-pyrimidin-4-one In a 500 mL round bottom flask equipped with an overhead stirrer and reflux condenser a solution of N-methylthiourea (15.56 g, 167.4 mmol) and diethyl 2-phenylmalonate (42.38 g, 175.8 mmol) under $N_2$ at 20° C. was prepared. Then to this solution was dosed $NaOCH_3$ (31.56 g, 175.8 mol, 30 wt % solution in methanol) over 2 h, during which a suspension formed. The reaction was stirred a further 48 h at 20° C., and then a solution of 2-chloro-1-(2-chlorothiazol-5-yl)ethanone (35.8 g, 180.0 mmol) in ethanol (204 g, 444 mol) was dosed over 2 h. The reaction was stirred at 20° C. for 48 h after addition was complete, and then cooled to 20° C. The formed solid was isolated via filtration in a fritted funnel. The filtercake was washed with 100 mL of ethanol three times, until the filtrate ran colorless. The filtercake was then returned to the reactor and slurried with 400 g of water at 70° C. for 1 h. The slurry was then filtered a fritted funnel, and the filtercake washed three times with 40 mL of room temperature water, and then dried at 80° C. and 5 mbar in a vacuum drying oven to afford 43.3 g (65% yield) of the title compound in form of a cream colored solid.

Example 5: Preparation of 2-[2-(2-chlorothiazol-5-yl)-2-oxo-ethyl]sulfanyl-6-hydroxy-3-methyl-5-phenyl-pyrimidin-4-one 10 g of N-methylthiourea (97%, 1.0 eq) and 28.5 g of diethyl 2-phenylmalonate (98%, 1.1 eq) were mixed and heated to 50° C. 21.3 g of sodium methylate (30% in methanol, 1.1 eq) were added and the reaction mixture was stirred at reflux for 12 h. 26.4 g of 2-chloro-1-(2-chlorothiazol-5-yl) ethanone, dissolved in 90 g of toluene, were dosed in 1 h and the reaction mixture was stirred at reflux for 10 h. After cooling to room temperature, 150 g of water were added, and the mixture was stirred for 2 h. The precipitate was filtered, and the filtercake washed with toluene (2×50 g). The solid was suspended in water (120 g) and stirred for 3 h, filtered and washed with water (100 g). The product was dried in vacuo overnight, yielding 40.0 g (98%, 92% yield) of the title compound.

Example 6: Preparation of 2-[2-(2-chlorothiazol-5-yl)-2-oxo-ethyl]sulfanyl-6-hydroxy-3-methyl-5-phenyl-pyrimidin-4-one 10 g of N-methylthiourea (97%, 1.0 eq) and 28.5 g of diethyl 2-phenylmalonate (98%, 1.1 eq) were dissolved in 25 g of methanol and heated to 50° C. 21.3 g of sodium methylate (30% in methanol, 1.1 eq) were added and the reaction mixture was stirred at reflux for 12 h. 26.4 g of 2-chloro-1-(2-chlorothiazol-5-yl)ethanone, dissolved in 75 g of dimethyl acetamide, were added and the reaction mixture was stirred at 70° C. for 15 h. 200 g of water were added, and the mixture was cooled to 20° C. The precipitate was filtered, and the filtercake was washed with water (400 g). The product was dried in vacuo overnight, yielding 44.0 g (93%, 96% yield) of the title compound.

Example 7: Preparation of 2-[2-(2-chlorothiazol-5-yl)-2-oxo-ethyl]sulfanyl-6-hydroxy-3-methyl-5-phenyl-pyrimidin-4-one 10 g of N-methylthiourea (97%, 1.0 eq) and 23.7 g of dimethyl 2-phenylmalonate (99%, 1.05 eq) were dissolved in 100 g of methanol at 25° C. 21.3 g of sodium methylate (30% in methanol, 1.1 eq) were added and the reaction mixture was heated to reflux over time. 28.9 g of 2-chloro-1-(2-chlorothiazol-5-yl)ethanone (95% 1.3 eq), dissolved in 70 g of methanol, were added at 50° C., the reaction mixture was further diluted with 150 g of methanol and stirred for 15 h. After cooling to room temperature, the precipitate was filtered off and washed with 2×50 g water. The filtercake was transferred to a flask and 400 g water added. The suspension was stirred for 1 h, filtered and the filtercake washed with water (2×50 g). The product was dried in vacuo overnight, yielding 36.5 g (98%, 85% yield) of the title compound.

Example 8: Preparation of 2-[2-(2-chlorothiazol-5-yl)-2-oxo-ethyl]sulfanyl-6-hydroxy-3-methyl-5-phenyl-pyrimidin-4-one with Isolation of Intermediate Compound 3

8.1 Preparation of the Intermediate 3, Wherein $M^+$ is $Na^+$

To a solution of methylthiourea (20.0 g, 218.7 mmol) and sodium methylate (42.6 g, 236.7 mmol, 30% solution in methanol used) and methanol (20 g) at 25° C. was added diethyl-2-phenylpropanedioate (57.1 g, 236.7 mmol). The reaction was then heated 70° C. for 6 h. Then the reaction was cooled to 25° C., upon which a precipitate formed. The precipitate was isolated by filtration, and the filtercake was triturated with methyl tert-butyl ether (100 g), filtered, and then dried at 100° C. for 48 h to afford the title compound as a light brown solid.

$^1H$ NMR (400 MHz, DMSO-d6): δ=10.62 (s, 1H), 7.70 (dd, 2H, J=1.33, 8.37 Hz), 7.13 (dd, 2H, J=7.11, 8.35 Hz), 6.98-6.90 (m, 1H), 3.50-3.47 (m, 1H), 3.50-3.47 (s, 3H), 3.21-3.15 (m, 1H)

8.2 Preparation of 2-[2-(2-chlorothiazol-5-yl)-2-oxo-ethyl]sulfanyl-6-hydroxy-3-methyl-5-phenyl-pyrimidin-4-one To a suspension of intermediate 3 wherein $M^+$ is $Na^+$(20.0 g, 69.45 mmol) as obtained in step 8.1 in methanol (50 g) at 75° C. was added a solution of 2-chloro-1-(2-chlorothiazol-5-yl) ethenone (16.2 g, 81.97 mmol) in methanol (50 g) over 30 min. The reaction was stirred at 50° C. for 3 h. Then the reaction was cooled to 50° C., and water (50 g) was added over 15 min. The reaction was then stirred for 2 h at 50° C., and then cooled to 25° C. and stirred for 30 min where a suspension formed. Water (100 g) was added and the formed solid was isolated by filtration. The filtercake was washed with water (100 g) and dried at 80° C. for 18 h in vacuo to afford the title compound as a brown solid (27.4 g, 95% yield).

Example 9: Preparation of 2-[2-(2-chlorothiazol-5-yl)-2-oxo-ethyl]sulfanyl-6-hydroxy-3-methyl-5-phenyl-pyrimidin-4-one In a 500 mL round bottom flask equipped with an overhead stirrer and reflux condenser a solution of N-methylthiourea (47.5 g, 500 mmol) and diethyl 2-phenylmalonate (125.9 g, 525 mmol) and chlorobenzene (60 g) under N2 at 60° C. was prepared. To this solution was dosed $NaOCH_3$ (99.1 g, 550 mmol, 30 wt % solution in methanol) over 30 min. The reaction was stirred for a further 16 h at 60° C., during which a suspension formed. Then the temperature was increased to 70° C. and a solution of 2-chloro-1-(2-chlorothiazol-5-yl) ethanone (115.6 g, 560 mmol) in chlorobenzene (230 g) was dosed over 2 h. The reaction was stirred at 70° C. for 2 h after addition was complete, and then cooled to 20° C. Water (460 g) was added and the mixture was stirred 1 h at 20° C., upon which a suspension formed. The formed solid was isolated via filtration in a fritted funnel. The filtercake was washed with 35 g of chlorobenzene three times, until the filtrate ran colorless. The filtercake was washed two times with 225 g of water, and then dried at 80° C. and 5 mbar in a vacuum drying oven for 48 h to afford 164 g (83% yield) of the title compound in form of a light brown colored solid.

Example 10: Preparation of 2-[2-(2-chlorothiazol-5-yl)-2-oxo-ethyl]sulfanyl-6-hydroxy-3-methyl-5-phenyl-pyrimidin-4-one In a 500 mL round bottom flask equipped with an overhead stirrer and reflux condenser a solution of N-methylthiourea (7.78 g, 83.7 mmol) and $KOCH_3$ (24.7 g, 87.9 mmol, 25 wt % solution in methanol) and methanol (4 g) under $N_2$ at 60-65° C. was prepared. Then diethyl 2-phenylmalonate (21.21 g, 87.9 mmol) was dosed over 30 min. The reaction was stirred a further 16 h at 65° C., during which a suspension formed; then a solution of 2-chloro-1-(2-chlorothiazol-5-yl)ethanone (18.6 g, 90.0 mmol) in ethanol (100 g) was dosed over 1 h. The reaction was cooled to 50° C. and stirred at 50° C. for 16 h after addition was complete. Then the reaction was cooled to 20° C. and the formed solid was isolated via filtration in a fritted funnel. The filtercake was washed with 50 g of ethanol three times, until the filtrate ran colorless. The filtercake was then returned to the reactor and slurried with 150 g of water at 75° C. for 1 h. The slurry was then filtered with a fritted funnel, and the filtercake washed three times with 40 mL of room temperature water, and dried at 90° C. and 5 mbar in a vacuum drying oven to afford 29.4 g (89% yield) of the title compound in form of a cream colored solid.

Example 11: Preparation of 2-[2-(2-chlorothiazol-5-yl)-2-oxo-ethyl]sulfanyl-6-hydroxy-3-methyl-5-phenyl-pyrimidin-4-one In a 500 mL round bottom flask equipped with an overhead stirrer and reflux condenser a solution of N-methylthiourea (15.56 g, 167.4 mmol) and $NaOCH_3$ (31.56 g, 175.8 mol, 30 wt % solution in methanol) under $N_2$ at 60° C. was prepared. Then to this solution was dosed diethyl 2-phenylmalonate (42.38 g, 175.8 mmol) over 30 min, during which a suspension formed. The reaction was stirred a further 10 h at 60° C., and then a solution of 2-chloro-1-(2-chlorothiazol-5-yl)ethanone (35.8 g, 180.0 mmol) in ethanol (204 g, 444 mol) was dosed over 6 h. The reaction was stirred at 60° C. for 8 h after addition was complete, and then cooled to 20° C. The formed solid was isolated via filtration in a fritted funnel. The filtercake was washed once on with 100 mL of ethanol followed by 2 washes with 400 g of water at 70° C. for 1 h and then dried at 100° C. and 5 mbar in a vacuum drying oven to afford 60.4 g (92% yield) of the title compound in form of a cream colored solid in 99 wt % purity.

The invention claimed is:

1. A method for preparing 2-[2-(2-chlorothiazol-5-yl)-2-oxo-ethyl]sulfanyl-6-hydroxy-3-methyl-5-phenyl-pyrimidin-4-one of formula (I):

(I)

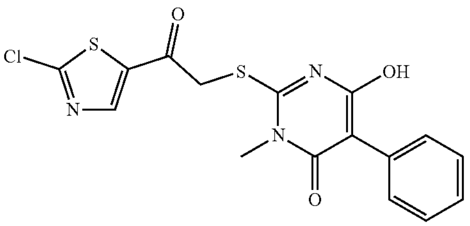

or a tautomer thereof, which method comprises (a) reacting N-methylthiourea of formula 1 with a 2-phenylmalonate of formula 2 in the presence of a base

1

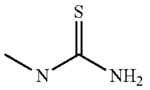

2

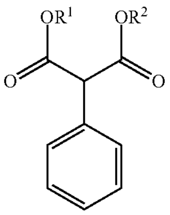

where $R^1$ and $R^2$, independently of each other, are $C_1$-$C_4$-alkyl;

to obtain a reaction mixture containing a pyrimidinone compound of formula 3

3

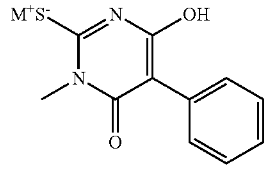

wherein $M^+$ is a cation equivalent;

and/or a tautomer thereof;

(b) optionally isolating the pyrimidinone compound of formula 3 or a tautomer thereof from the reaction mixture obtained in step (a) either in a form of its salt or in a thiol form; and (c) reacting either the reaction mixture obtained in step (a) without isolation of the pyrimidinone compound of formula 3 or its tautomer or the compound obtained in step (b) with 1-(2-chlorothiazol-5-yl) ethanone of formula 4

4

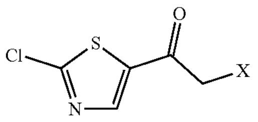

where X is a leaving group, to obtain the compound of formula (I) or a tautomer thereof.

2. The method according to claim 1, where $R^1$ and $R^2$, independently of each other, are methyl or ethyl.

3. The method according to claim 1, where the base used in step (a) is selected from the group consisting of alkali metal $C_1$-$C_4$-alkanolates, alkali metal carbonates, earth alkaline metal carbonates, alkali metal hydroxides, earth alkaline metal hydroxides, alkali metal phosphates, non-nucleophilic organic bases, and mixtures thereof.

4. The method according to claim 3, where the base used in step (a) is selected from the group consisting of sodium methanolate, sodium ethanolate, sodium isopropanolate, sodium tert-butanolate, potassium methanolate, potassium ethanolate, potassium tert-butanolate, lithium methanolate, and mixtures thereof.

5. The method according to claim 1, where in step (a) the 2-phenylmalonate 2 is used in an amount of from 0.8 to 2.0 mol per mol of N-methylthiourea 1.

6. The method according to claim 1, where in step (a) the base is used in an amount of from 0.8 to 1.5 mol per mol of N-methylthiourea 1.

7. The method according to claim 1, where the reaction in step (a) and (c) is carried out in a solvent selected from the group consisting of polar protic solvents, polar aprotic solvents, $C_1$-$C_4$-alkyl acetates, dialkyl ethers, aromatic solvents, heterocyclic solvents, and mixtures thereof.

8. The method according to claim 7, where the solvent is selected from the group consisting of methanol, ethanol, n-propanol, isopropanol, isobutanol, tert-butanol, tetrahydrofuran, 2-methyltetrahydrofuran, 1,4-dioxane, dimethylformamide, dimethylacetamide, toluene, chlorobenzene, N-methylpyrrolidone, and mixtures thereof.

9. The method according to claim 8, where step (a) is carried out in a solvent selected from the group consisting of methanol, ethanol, a mixture of methanol and ethanol, and a mixture of methanol and/or ethanol with at least one further solvent which is selected from the group consisting of dimethylacetamide, toluene, and chlorobenzene, and step (c) is carried out in a solvent selected from the group consisting of methanol, ethanol, dimethylacetamide, toluene, chlorobenzene, and mixtures of at least two of the aforementioned solvents.

10. The method according to claim 1, where in step (c) the reaction mixture obtained in step (a) is reacted with the compound of formula 4.

11. The method according to claim 1, where X in the compound of formula 4 is selected the group consisting of halogen, triflate, mesylate, tosylate and nonaflate.

12. The method according to claim 11, where X in the compound of formula 4 is Cl.

13. The method according to claim 1, where in step (c) the 1-(2-chlorothiazol-5-yl) ethanone 4 is used in an amount of from 0.8 to 1.5 mol per mol of N-methylthiourea 1 used in step (a).

14. The method according to claim 1, where step (c) is carried out in the presence of an additive selected from the group consisting of alkali metal bromides, alkali metal iodides, ammonium bromides, ammonium iodides, and mixtures thereof where the additive is used in an amount such that a molar ratio of additive and 2-chloro-1-(2-chlorothiazol-5-yl) ethanone 4 is in a range of from 1:100 to 10:1.

15. 2-[2-(2-Chlorothiazol-5-yl)-2-oxo-ethyl] sulfanyl-6-hydroxy-3-methyl-5-phenyl-pyrimidin-4-one of the formula (I):

(I)

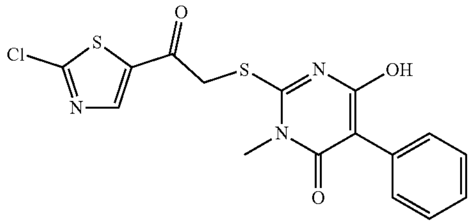

or a tautomer thereof.

16. The method according to claim 2 where $R^1$ and $R^2$ are both methyl or are both ethyl.

17. The method of claim 7 where the solvent is selected from the group consisting of $C_1$-$C_4$-alkanols, glycols, tetrahydrofuran, 2-methyltetrahydrofuran, a dioxane, dimethylformamide, dimethylacetamide, dimethylsulfoxide, $C_1$-$C_4$-alkyl acetates, di-n-propyl ether, di-n-butyl ether, methyl-tert-butyl ether, acetonitrile, benzene, toluene, a xylene, chlorobenzene, dichlorobenzene, N-methylpyrrolidone, and mixtures thereof.

18. The method of claim 14 where the additive is selected from the group consisting of NaBr, KBr, NaI, KI, tetrabutylammonium bromide, and mixtures thereof.

* * * * *